United States Patent [19]
Capozza

[11] 4,074,366
[45] Feb. 21, 1978

[54] POLY(N-ACETYL-D-GLUCOSAMINE) PRODUCTS

[75] Inventor: Richard Carl Capozza, Norwalk, Conn.

[73] Assignee: American Cyanamid Company, Stamford, Conn.

[21] Appl. No.: 707,912

[22] Filed: July 22, 1976

Related U.S. Application Data

[62] Division of Ser. No. 558,525, March 14, 1975, Pat. No. 3,989,535, which is a division of Ser. No. 441,717, Feb. 11, 1974, abandoned, which is a division of Ser. No. 558,526, March 14, 1975, Pat. No. 3,988,411.

[51] Int. Cl.² ............................................. A61F 1/00
[52] U.S. Cl. ............................................. 3/1; 424/180
[58] Field of Search ............... 3/1; 128/92 C; 424/180

[56] References Cited

U.S. PATENT DOCUMENTS

| 3,605,123 | 9/1971 | Hahn | 3/1 |
| 3,632,754 | 1/1972 | Balassa | 424/180 |
| 3,878,284 | 4/1975 | Schmitt et al. | 260/33.4 R |
| 3,879,377 | 4/1975 | Austin | 424/180 |
| 3,892,731 | 7/1975 | Austin | 424/180 |
| 3,903,268 | 9/1975 | Balassa | 424/180 |
| 3,914,413 | 10/1975 | Balassa | 424/180 |

Primary Examiner—Leland A. Sebastian
Attorney, Agent, or Firm—Charles F. Costello, Jr.

[57] ABSTRACT

Poly(N-acetyl-D-glucosamine) is soluble in hexafluoroisopropyl alcohol and hexafluoracetone sesquihydrate. The solutions formed may be wet or dry spun into filaments, or cast into films or solid articles, which may be used as absorbable surgical sutures, or other absorbable surgical elements. Poly(N-acetyl-D-glucosamine) is enzymatically degradable in living tissue, and is resistant to hydrolytic degradation, and, therefore, surgical elements thereof have good storage characteristics under a wide variety of conditions.

3 Claims, No Drawings

POLY(N-ACETYL-D-GLUCOSAMINE) PRODUCTS

This is a division, of application Ser. No. 558,525, filed Mar. 14, 1975, U.S. Pat. No. 3,989,535, which is a division of application Ser. No. 441,717, filed Feb. 11, 1974 now abandoned. Another divisional of said Ser. No. 441,717 is application Ser. No. 558,526, filed Mar. 14, 1975, U.S. Pat. No. 3,988,411.

BACKGROUND OF THE INVENTION

Poly(N-acetyl-D-glucosamine) is a known polymer which is a component of naturally occurring chitin. It is regarded as insoluble in conventional solvents, and, therefore, has been used as a powder. There is a demand for absorbable surgical elements, particularly sutures, which are strong enough to serve as a tissue retaining element during a healing process, and which then are absorbed by the living tissue. Requirements for the duration of useful strength vary widely with both the type of tissue and the surgical procedure. Some cosmetic purposes require strength for only a few hours or a few days. Other uses require strength for periods of months or even years. Advantageously, the surgical element should absorb promptly after it has served its useful function. Sutures have long been treated with dyes and therapeutic agents, poly(N-acetyl-D-glucosamine) sutures may be so treated.

Absorbable surgical elements usually start losing strength almost as soon as implanted, but a useful degree of strength is maintained for a much longer period. Complete absorption is, of course, much slower. Sharp changes in strength with time are not to be expected.

DESCRIPTION OF THE PRIOR ART

U.S. Pat. No. 3,297,033, Schmitt and Polistina, Jan. 10, 1967, SURGICAL SUTURES, discloses polyhydroxyacetic ester absorbable sutures. The material is also called polyglycolic acid, and is disclosed as permitting small quantities of comonomers to be present, such as dl-lactic acid, its optically active forms, homologs and analogs. A small quantity is recognized by the art as up to 15%, as shown by U.S. Pat. No. 2,668,162, Lowe, Feb. 2, 1954, PREPARATION OF HIGH MOLECULAR WEIGHT POLYHYDROXY-ACETIC ESTER.

Many uses of polyglycolic acid for surgical purposes are disclosed in said U.S. Pat. No. 3,297,033 and continuations-in-part thereof including: U.S. Pat. No. 3,463,158, Schmitt and Polistina, Aug. 26, 1969, POLYGLYCOLIC ACID PROSTHETIC DEVICES; U.S. Pat. No. 3,620,218, Schmitt and Polistina, Nov. 16, 1971, CYLINDRICAL PROSTHETIC DEVICES OF POLYGLYCOLIC ACID; U.S. Pat. No. 3,739,773, Schmitt and Polistina, June 19, 1973, POLYGLYCOLIC PROSTHETIC DEVICES; and U.S. Ser. No. 365,656, Schmitt and Polistina, May 31, 1973, SURGICAL DRESSINGS OF ABSORBABLE POLYMERS.

U.S. Pat. No. 3,463,158, Schmitt and Polistina, Aug. 26, 1969, POLYGLYCOLIC ACID PROSTHETIC DEVICES, discloses surgical uses of polyglycolic acid, and incorporates definitions of some terms.

U.S. Pat. No. 3,620,218, Schmitt and Polistina, November 16, 1971, CYLINDRICAL PROSTHETIC DEVICES OF POLYGLYCOLIC ACID, lists many surgical uses of polyglycolic acid.

U.S. Pat. No. 3,737,440, Schmitt and Bailey, June 5, 1973, POLYGLYCOLIC ACIDS IN SOLUTIONS, discloses hexafluoroisopropyl alcohol and hexafluoroacetone sesquihydrate as solvents for the preparation of solutions of polyglycolic acid, and wet and dry casting of such solutions. Polyglycolic acid has many surgical uses as an absorbable polymer.

Polyglycolic acid sutures are the only synthetic absorbable sutures that have met with commercial surgical acceptance to date.

Chitin has been estimated to be the second most abundant polysaccharide in nature with a synthesis in the neighborhood of a billion tons a year by marine organisms. See Chitin, N. V. Tracey, Reviews of Pure and Applied Chemistry, Royal Australian Chemical Institute, Vol. 7, No. 1, March, 1957, pages 1 to 14.

Carboxymethylchitin is disclosed in Carbohyd, Res. 7, 483–485 (1968), Ralph Trujillo.

This article mentions the hydrolysis of both chitin and carboxymethylchitin by lysozyme.

I. Joffe and H. R. Hepburn, "Observations on Regenerated Chitin Films," J. Materials Science, 8 (1973), 1751–1754, give values on the strength of films of regenerated chitin, from a chitin xanthate dispersion — including a comparison of strength after 30 years storage. Values as high as $9.31 \times 10^7 Nm^{-2}$ are given (calculates to $6.3 \times 10^3$ pounds/sq. inch).

Noguchi, Wada, Seo, Tokura and Nishi, "Studies on Chitin and Chitin-Cellulose Fibers," Kobunshi Kagaku, Vol. 30, No. 338, pp. 320–326 and 378, (June 1973) disclose chitin fibers spun by a xanthate process, analogous to the spinning of cellulose to form rayon. A 50% chitin-cellulose fiber is disclosed with a denier of 12.3 and a tenacity of 1.08 grams/denier dry and 0.13 grams/denier wet.

Poly(N-acetyl-D-glucosamine) differs from cellulose in that instead of a hydroxyl group in the 2 position on cellulose, there is an acetylamino group.

Prudden, Migel, Hanson, Freidrich and Balassa in "The Discovery of a Potent Pure Chemical Wound-Healing Accelerator," The American Journal of Surgery, Vol. 119, May 1970, pages 560 to 564, disclose that chitin containing n-acetyl glucosamine is useful to accelerate wound-healing. These authors postulate fibers of a long chain n-acetyl glucosamine as a nonabsorbable suture, and a shorter polymer length as an absorbable suture. Other prosthetic devices, such as hemostatic clips, vascular and joint protheses, mesh and knit abdominal thoracic wall replacements are postulated for evaluation. No methods are postulated for the achievements of these objectives.

The above patents and articles are herein hereby incorporated by this reference thereto for background information on chitin, its properties and derivatives.

SUMMARY OF THE INVENTION

This invention relates to solid surgical elements of poly(N-acetyl-D-glucosamine), methods of making them, and more particularly to polymers which are compatible with living mammalian tissue, particularly human tissue, and which can be used surgically, and are biologically degradable into tissue compatible components which are absorbed by living tissues. The primary degradation of the polymer is by enzymatic fission into products which can be carried away by the living tissue and which products are degradable to excretable components or are themselves excretable. Because of the surgical demand for sutures, absorbable fabrics, gauzes, bone pins, etc. whose absorption and strength characteristics vary, it is desirable that a spectrum of strength and absorbability characteristics be provided to meet surgical demands for various procedures. The enzyme lysozyme is particularly effective in the enzymatic degradation of poly(N-acetyl-D-glucosamine). Various forms of poly(N-acetyl-D-glucosamine) may have different degradation rates, and the degradation rate may vary with the location.

Poly(N-acetyl-D-glucosamine) has many advantages as a material of construction for sutures and other surgical elements. The poly(N-acetyl-D-glucosamine) in its own right tends to encourage wound healing rather than slow it down. Poly(N-acetyl-D-glucosamine) is biodegradable by enzymatic action with minimal tissue reaction.

Surgical elements of poly(N-acetyl-D-glucosamine) are not hydrolyzed by water and, hence, need not be kept bone dry but may be stored under ambient conditions of moisture for prolonging periods of time. The basic poly(N-acetyl-D-glucosamine) may be modified by treatment to introduce carboxymethyl, hydroxyethyl or O-ethyl substituents so that the polymer has linkages from acetyl-6-O-(carboxymethyl)-D-glucosamine units, acetyl-6-O-(2'-hydroxyethyl)-D-glucosamine units, or acetyl-6-O-(ethyl)-D-glucosamine units. Since modification by the introduction of these derivatives alters the rate of enzymatic degradation, such introduction provides a means for controlling the absorption rate as well as making the surgical element more hydrophilic or more hydrophobic to an extent desire.

Other side chains may be placed on the glucosamine ring, or its substituents because the side chains may vary from methyl to long chain alkyl, including branched chains, unsaturated chains, aryl or aralkyl, and which may include halogen, alkoxy, aryloxy, aralkoxy, ether, ester and amide groups, as substituents on the side chains, the relative distribution between aqueous and solvent components in a system can be varied as well as water solubility or oil and solvent solubility. Also, because the size and location of the side chains affects the rate of degradation and the acidity of the system, the rate of enzymatic degradation can be varied over wide limits to meet the requirements of a system and the desires of the operator. The less highly substituted materials are often preferred for medical uses. The broader range of substituents permits more flexibility in pH control, and in biodegradable polymers for use in packaging, etc. The use of side chains with unsaturated linkages permits crosslinked polymers to be formed. This uniformity results in greater strength, more crystallinity, and more readily reproducible and controllable characteristics, which are of interest to a surgeon during use.

Fibers made by extruding solutions of poly(N-acetyl-D-glucosamine) in polyfluorinated solvents such as hexafluoroisopropyl alcohol and hexafluoroacetone sesquihydrate or mixtures of such solvents permit dry or wet spinning of fibers which are of a convenient size for forming sutures.

The fibers are more pliable when wet with water. The enhanced pliability, when wet with water, is highly advantageous in that many surgeons are accustomed to handling catgut which must be wet with water to have adequate handleability and, hence, are using familiar techniques and procedures in surgery. Monofilaments are usable when wet. A dry braided construction of polyfilamentary character is frequently advantageous.

Poly(N-acetyl-D-glucosamine) has the formula:

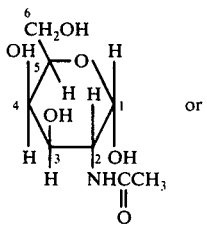

or

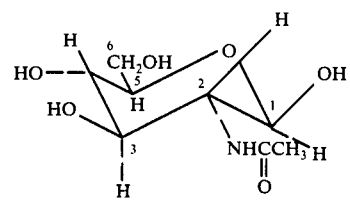

Groups below the plane of the paper are shown by a dotted bond.

Poly(N-acetyl-D-glucosamine) has ascribed to it the formula (ring hydrogens omitted for clarity):

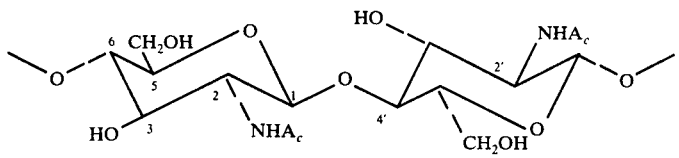

Poly(N-acetyl-D-glucosamine) is a major component of naturally occurring chitin. The naturally occurring material has not only the poly(N-acetyl-D-glucosamine) but also inorganic salts thought to be forms of calcium carbonate and proteinaceous material, the composition of which is not presently known. The term "chitin" is used herein to refer to the various naturally occurring forms of chitin including the protein and inorganic carbonate components. The term "purified chitin" is used to refer to chitin after purification to remove calcium carbonate and other inorganic salts and various proteins which may be present and is essentially poly(N-acetyl-D-glucosamine). Some confusion exists in the literature in that the name chitin is used as a name for poly(N-acetyl-D-glucosamine) without specifying whether it is a naturally occurring material containing inorganic salts and proteins or whether the term is intended to designate purified poly(N-acetyl-D-glucosamine) without specifying the degree of purity or the character of the impurities present.

The term "drug" is used to refer to a substance other than a food intended to affect the structure or function of the body of man or other animal. The term is somewhat broader than "medicine" in that the term "medicine" is sometimes considered to be restricted to an agent which is administered to affect or control a pathogenic condition.

The term "enzymatically degradable" refers to a form of poly(N-acetyl-D-glucosamine) or its derivatives which is broken down into body fluid soluble components. The problem of retention by the body or disposal of the residual matrix is minimal or non-existent.

While other enzymes may also affect the enzymatic degradation of the poly(N-acetyl-D-glucosamine) matrix, the enzyme which is most widely distributed in the body and here very effective is lysozyme. Lysozyme occurs in practically all of the body fluids and effectively breaks down the polymer chain to water soluble or disposable components.

Poly(N-acetyl-D-glucosamine) is not readily hydrolyzed by water.

It is highly advantageous to have the degradation of the poly(N-acetyl-D-glucosamine) occur only by the action of an enzyme as the resistance to hydrolytic degradation markedly reduces problems of manufacture and storage in the presence of ambient moisture, and ensures a steady smooth surface erosion rather than a fragmentation process commonly experienced by polymers which are hydrolyzed by small molecules.

The degradation rate of poly(N-acetyl-D-glucosamine) can be lowered by crosslinking, if a slower rate is preferred.

In general, the surgical uses of the polymers of the present invention are similar to those previously taught for polyglycolic acid and as set forth in U.S. Pat. Nos. 3,297,033; 3,463,158; 3,620,218; and 3,739,773, and U.S. Ser. No. 365,656, supra. These disclosures of uses are herein hereby incorporated by this reference thereto.

These uses are extremely varied. For clarity and explanation, certain terms are defined and representative uses given for the novel polymer forms.

A "filament" is a single, long, thin flexible structure of a non-absorbable or absorbable material. It may be continuous or staple.

"Staple" is used to designate a group of shorter filaments which are usually twisted together to form a longer continuous thread.

An absorbable filament is one which is absorbed, that is, digested or dissolved, in living mammalian tissue.

A "thread" is a plurality of filaments, either continuous or staple, twisted together.

A "strand" is a plurality of filaments or threads twisted, plaited, braided, or laid parallel to form a unit for further construction into a fabric, or used per se, or a monofilament of such size as to be woven or used independently.

A "fabric" is a three dimensional assembly of filaments, which may be woven, knitted, felted or otherwise formed into a flexible sheet having two layer dimensions and a thinner thickness dimension. A fabric may be cut to a desired size before or at the time of use.

Except where limited specifically or by context, the word fabric includes both absorbable and non-absorbable cloth, or a fabric or cloth that is partially of absorbable polymer.

A "dressing" is a woven, knitted, felted or braided fabric, of at least one layer, which is designed to protect a wound and favor its healing. As used herein, the term dressing includes bandages, insofar as they contact the wound itself. The dressing may be entirely internal.

A "bandage" is a strip of gauze, or other material used to hold a dressing in place, to apply pressure, to immobilize a part, to obliterate tissue cavities or to check hemorrhage. Except insofar as the bandage comes in contact with a wound, or the exudate from a wound, there is no need for the bandage to be of absorbable polymer. If the bandage may be in a position where absorbability by living tissue of at least part of the bandage is desirable, at least that part should be of absorbable polymer.

The dressing may be in part directive of growth, as, for example, in nerve tissue, which grows slowly, and as a result has regeneration impaired by the more rapid growth of scar tissue which can block the growth of the nerve tissue. With a wrap-around sheath of absorbable polymer fabric or a split or solid tube used to support, place, hold and protect; regeneration of nerve tissue and function is greatly aided. Other factors may inhibit regeneration of nerve tissue or function, but with the exclusion of scar tissue, such other factors may be separately treated.

For different purposes and in different types of tissue the rate of absorption may vary. In general, an absorbable suture or solid load bearing prosthesis should have as high a portion of its original strength as possible for at least 3 days, and sometimes as much as 30 days or more, and preferably should be completely absorbed by muscular tissue within from 45 to 90 days or more depending on the mass of the cross-section. The rate of absorption in other tissues may vary even more.

For dressings, strength is often a minimal requirement. Some dressings, as for instance, on a skin abrasion, may need strength for only a few hours, until a scab forms, and rapid decrease of strength and absorption is an advantage so that when the scab is ready to fall off, the dressing does not cause a delay. For burns, and larger lesions, strength and reinforcement may be desired for a longer period.

In common with many biological systems, the requirements are not absolute and the rate of absorption as well as the short-term strength requirement varies from patient to patient and at different locations within the body, as well as with the thickness of the section of the polymer.

The absorbable polymer may be formed as tubes or sheets for surgical repair and may also be spun as thin filaments and woven or felted to form absorbable sponges or absorbable gauze, or used in conjunction with other compressive structures as prosthetic devices within the body of a human or animal where it is desirable that the structure have short-term strength, but be absorbable. The useful embodiments include tubes, including branched tubes or Tees, for artery, vein or intestinal repair, nerve splicing, tendon splicing, sheets for tying up and supporting damaged kidney, liver and other intestinal organs, protecting damaged surface areas such as abrasions, particularly major abrasions, or areas where the skin and underlying tissues are damaged or surgically removed.

In surgical techniques involving internal organs, hemorrhage may be a major problem. Some of the organs have such tissue characteristics that it is very difficult to use sutures or ligatures to prevent bleeding. For example, the human liver may suffer traumatic damage or exhibit tumors or for other reasons require surgery. In the past it has been very difficult to excise part of the liver or to suture the liver without the combined problems of the sutures cutting out and hemorrhage at the surface causing such major complications as to either prevent surgery or cause an unfavorable prognosis.

It is now found that a sponge or pad or velour of the present absorbable polymer may be used to protect the surface and permit new feats of surgical intervention. For instance, filaments may be formed into a woven gauze or felted sponge or a velour, preferably the construction is fairly tight by textile standards, and such sponge may be placed on the surface of the bleeding organ such as the liver or a lung with either gentle suturing or with ties in the nature of ligatures to hold the element in position with a certain amount of body fluids flowing into the sponge and being absorbed, which results in hemostasis and prevention of further loss of body fluids. If a liver or lung is so repaired, the organ may be replaced in the body cavity and the wound closed.

Where surgically useful, the sponge or fabric can be used as a bolster to prevent a suture from cutting out. For instance, if the liver is to be sutured, an absorbable polymer pad can be placed on the surfaces to reinforce the tissue and prevent the suture from cutting into rather than retaining the tissue. Such pads of gauze or felt protect tissue from cutting.

Absorbable pads, bandages or sponges are extremely useful in surgical techniques in which it is the intent to remove the major portion or all of such sponges, felt or pads but, through inadvertence or accident, part of it may remain. For instance, in a surgical operation one of the problems which arises is the lint from cotton sponges remaining in the wound. If absorbable polymer sponges are used, any small fragments which are accidentally displaced are absorbed without incident and even if a sponge is left in the wound, the deleterious effects are minimal.

The use of a synthetic absorbable polymer as a sponge or pad is particularly advantageous for surface abrasions. In the past it has been necessary to put on a dressing and avoid having the non-absorbable dressing grow into the tissue at all costs. If elements of an absorbable polymer gauze are beneath the regenerating tissue level, the tissue will regenerate and absorb the polymer with the residual polymer in the scab falling off when the scab is displaced.

The dressing that contacts tissue should be sterile. A strippable sterile package is a convenient storage system to maintain sterility between the time of manufacture and time of use.

Even in cosmetic surgery or skin surgery, where in the past it has been quite customary to use silk sutures and, after the tissue in regenerated sufficient to be self-retaining, remove the sutures so that they do not leave scars, the use of synthetic absorbable polymer sutures now permits implantation of sutures through the skin with the part below the skin surface being absorbed and the part above the skin surface falling off. The resulting minimal degree of scarring at the skin surface is highly advantageous.

In surgery various tissues need to be retained in position during healing. Defects and wounds of the abdominal wall, chest wall and other such tissues need to be reconstructed. For a hernia, a permanent splice or reinforcement is often desired as shown in Usher, U.S. Pat. No. 3,054,406, SURGICAL MESH, or U.S. Pat. No. 3,124,136, METHOD OF REPAIRING BODY TISSUE. For some surgical procedures, a temporary reinforcing is desired to provide strength while body tissues are healing; and after the body tissues have assumed the load, foreign components are no longer desired. Tissue retention using the general techniques disclosed in the Usher patents, supra, are readily accomplished using either an absorbable synthetic polymer monofilament or polyfilament fabric or mesh or by using a non-absorbable material such as polyethylene or polypropylene or polyester woven as a bicomponent mesh or kit with an absorbable synthetic polymer. The use of a bicomponent fabric has the advantage of giving additional early strength for holding the tissues in position during initial regeneration with the absorbable portions being absorbed, thus permitting body tissues to invade and reinforce the permanent mesh.

In common with other surgical procedures, it is often desirable that a bicomponent structure be used which provides the spacing desired for non-absorbable elements, with the absorbable synthetic polymer element holding the structure in a desired geometrical configuration at the start of the healing process. As the element is absorbed, regenerating tissue invades and replaces the dissolved synthetic polymer so that the non-absorbed element is left in a desired configuration, interlaced with living tissue in a stress-transferring relationship.

The choice of a non-absorbable reinforcement, a partially absorbable reinforcement, or a completely absorbable reinforcement is a matter of surgical judgment, based upon the condition of the patient, the body structure under treatment, and other medical factors.

For instance, a synthetic absorbable polymer sponge may be used in a cavity after tooth extraction to stanch the flow of blood. The sponge is either absorbed by regenerating tissue, or disintegrates into the mouth, permitting improved recovery after extractions.

The medical uses of the polymers of the present invention include, but are not necessarily limited to:

A. Absorbable polymer alone

1. Solid Products, molded or machined
    a. Orthopedic pins, clamps, screws and plates
    b. Clips (e.g., for use as hemostat)
    c. Staples
    d. Hooks, buttons and snaps
    e. Bone substitute (e.g., mandible prosthesis)
    f. Needles
    g. Non-permanent intrauterine devices (spermicide)
    h. Temporary draining or testing tubes or capillaries
    i. Surgical instruments
    j. Vascular implants or supports
    k. Vertebral discs
    l. Extracorporeal tubing for kidney and heart-lung machines.
2. Fibrillar Products, knitted or woven, including velours
    a. Burn dressings
    b. Hernia patches
    c. Absorbent paper or swabs
    d. Medicated dressings
    e. Facial substitutes
    f. Gauze, fabric, sheet, felt or sponge for liver hemostasis
    g. Gauze bandages
    h. Dental packs
    i. Surgical sutures
3. Miscellaneous
    a. Flake or powder for burns or abrasions
    b. Foam as absorbable prosthesis
    c. Substitute for wire in fixations
    d. Film spray for prosthetic devices B. Absorbable polymer in Combination with other Products
1. Solid Products, molded or machined
   a. Slowly digestible ion-exchange resin
   b. Slowly digestible drug release device (pill, pellet) as a repository, oral or implanted or intravaginal
   c. Reinforced bone pins, needles, etc.
2. Fibrillar Products
   a. Arterial graft or substituents
   b. Bandages for skin surfaces
   c. Burn dressings (in combination with other polymeric films)
   d. Coated sutures (i.e., a coating on a suture of this polymer)
   e. A coating of the present polymer on a suture of other material
   f. A two component suture, one being the present polymer, the components being spun or braided together
   g. Multicomponent fabrics or gauzes, the other component of which may be non-absorbable, or more rapidly absorbable.

The synthetic character and hence predictable formability and consistency in characteristics obtainable from a controlled process are highly desirable.

One convenient method of sterilizing synthetic absorbable polymer prosthesis is by heat under such conditions that any microorganisms or deleterious materials are rendered inactive. Another common method is to sterilize using a gaseous sterilizing agent such as ethylene oxide. Other methods of sterilizing include radiation by X-rays, gamma rays, neutrons, electrons, etc., or high intensity ultrasonic vibrational energy or combinations of these methods. The present synthetic absorbable polymers may be sterilized by any of these methods, although there may be an appreciable but acceptable change in physical characteristics.

Other substances may be present, such as dyes, antibiotics, antiseptics, anaesthetics, and antioxidants. Surfaces can be coated with a silicone, beeswax, and the like to modify handling or absorption rate.

The absorbable polymer can be spun into fibers and used to form strands. Fibers of about 0.002 inch diameter are particularly convenient for fabrication. Sheets, or tubes from these absorbable polymer are wrapped around nerves, traumatically severed, to protect such nerves from invasive scar tissue growth, while the nerve is regenerating.

The ends or edges of mono-component or bi-component fabrics containing absorbable polymer may be rendered rigid by molding such edges, with or without additional solid absorbable polymer to a desired configuration. It is often easier to insert and retain a flexible fabric prosthetic tube if the end of the tube is of a size and shape to be inserted into the severed end of a vessel.

In the case of extensive superficial abrasions, dressings, frequently gauze, pads or wrappings absorb blood or lymph and present a problem because the gauze dressings stick to the wound or are infiltrated by regenerated tissue. In the past, it has been customary to change dressings frequently to prevent such infiltration. Removing an adherent dressing can be quite painful.

Extensive surface abrasions such as from sliding on a concrete surface after falling off a motorcycle can be debrided and wrapped with a gauze synthetic absorbable polymer. The wound shows a tendency to bleed into the absorbable polymer gauze but the porosity of the gauze aids in rapidly stopping the flow of blood. By using several layers and permitting the blood to at least partially harden, a minimum amount of the absorbable polymer gauze is required and the main protective dressing is of ordinary cotton gauze wrapped around the injured area. A minimum of changing the dressing is required. The outer cotton gauze may be removed for inspection to be sure that infection does not occur, but the absorbable polymer gauze is allowed to remain in position, and partly heals into the tissue, and partly remains above the tissue. Fewer manipulative steps aid in preventing the entrance of new pathogens. After healing, the gauze below the new skin surface absorbs in the body and the non-absorbed gauze and the scab separate readily.

Poly(N-acetyl-D-glucosamine) is reported to be insoluble in all solvents except 88% phosphoric acid which badly degrades the polymer. Unexpectedly, it has now been found that hexafluoroisopropanol (HIPA) and hexafluoroacetone sesquihydrate (HFAS) are solvents for poly(N-acetyl-D-glucosamine). The solutions are quite viscous at 1.5% concentration and transparent. Clear, transparent films that are tough and very pliable when wet can be cast from these two fluorinated solvents. The films are easily removed from glass when wet. There is the appearance of crystalline regions as indicated by birefringence under a polarizing microscope. There was no indication of any polymer degradation in these solvents by infrared spectroscopic and nuclear magnetic resonance spectroscopic examination of the films.

The concentration of solution employed depends in part upon the desired thickness of a desired film. Thicknesses of anywhere from 0.5 mil to about 50 mils can be readily prepared. The films are tough, self-supporting films. The polyfluorinated solvents may be removed by evaporation in air, under reduced pressure, or by using a solvent, such as acetone, to wash out the polyfluorinated solvent. The casting surface is conveniently glass but may be stainless steel, poly(tetra-fluoroethylene), or other fluorinated polymer, or non-stick surface — even a liquid.

Elevated temperatures may be used. Poly(N-acetyl-D-glucosamine) decomposes on heating at about 220° C but may be heated to lower temperatures to speed the removal of the polyfluorinated solvent.

The solutions of poly(N-acetyl-D-glucosamine) in hexafluoroisopropyl alcohol and hexafluoroacetone sesquihydrate may be spun into filaments by standard techniques for wet or dry spinning. In a typical wet-spinning operation a solution or spinning dope of poly(N-acetyl-D-glucosamine) in hexafluoroisopropyl alcohol or hexafluoroacetone sesquihydrate is extruded at a solution temperature from about room temperature up to about 60° C. through an appropriate orifice into a coagulated medium such as acetone or the solvents mentioned above. The coagulating liquid temperature may conveniently be at a temperature below that of the extrusion and may be very cold, well below 0° C. and may be any solvent or system in which the polymer coagulates and permits the ready removal of the solvent in the spinning dope.

It should be noted that although the boiling point of hexafluoroisopropyl alcohol is about 58° C. at atmospheric pressure, the boiling point of solutions of poly(N-acetyl-D-glucosamine) in hexafluoroisopropyl alcohol will exceed 58° C. depending upon how much polymer is dissolved in the solvent, and the pressure exerted on the system. Thus, solution temperatures and ranges of temperatures such as room temperature to 80° C. and similar ranges which appear throughout this specification contemplate the temperatures of solutions containing varying amounts of poly(N-acetyl-D-glucosamine) under pressures sufficient to elevate the boiling point of the solution into the upper limits of such temperature ranges.

Dilute solutions of poly(N-acetyl-D-glucosamine) in hexafluoroisopropyl alcohol and hexafluoroacetone sesquihydrate find utility as a vehicle for the measuring of viscosity and, hence, the determination of molecular weight and other physical characteristics of the polymer.

At the much thicker concentrations conveniently used for wet or dry spinning, the viscosity may become so high that extrusion is difficult and the extrudability with available equipment is a limiting factor on concentration.

The extrusion may be into the atmosphere, that is, dry spinning, with the hexafluoroisopropyl alcohol or hexafluoroacetone sesquihydrate being removed by evaporation. The fibers may be wound as they harden; care being used to insure that the surface of the fiber is sufficiently hard that spinning dope does not adhere to equipment. The final treatment stages may be at higher temperatures with the limiting factor being decomposition of the polymer. Drying under vacuum speeds removal of the last traces of the polyfluorinated solvents.

Poly(N-acetyl-D-glucosamine) may be obtained in fibrillar form by precipitating a solution thereof in toluene. For instance, a 1.5% solution of poly(N-acetyl-D-glucosamine) in hexafluoroacetone sesquihydrate is precipitated by pouring it into toluene. After drying, the material is similar in appearance and handling to dried cellulose pulp and is fibrilar in nature.

Fibers suitable for sutures and fabrics are manufactured by extruding a viscous solution of poly(N-acetyl-D-glucosamine) dissolved in hexafluoroisopropyl alcohol or hexafluoroacetone sesquihydrate into a solvent bath. Solvents such as acetone, water, isopropanol, ether, other lower alcohols and other lower ketones are volatile, liquid at extrusion temperatures and low in cost.

The concentration of the poly(N-acetyl-D-glucosamine) in polyfluorinated solvent may be varied widely. Solutions as dilute as 0.01% may be used but to avoid the use of excess quantities of the expensive polyfluorinated solvents, a concentration of about 0.5% to about 5% is usually preferred. Concentrations as high as 10% may be used, but at higher concentration, the solvent becomes quite viscous and it is often convenient to use a more dilute solution. Higher concentrations may be used if high pressure extruding equipment is available.

The extrusion is conveniently accomplished by wet extrusion into a solvent which aids in removing the hexafluoroisopropyl alcohol and hexafluoroacetone sesquihydrate from the polymer. By washing with solvent, particularly at above room temperature, the hexafluoroacetone sesquihydrate and hexafluoroisopropyl alcohol are removed from the filaments or films formed. Because both hexafluoroisopropyl alcohol and hexafluoracetone sesquihydrate are known to be toxic, these should be washed out of polymers which are to be implanted in living tissue. Small quantities of the polyfluorinated solvents can be detected by gas chromatography or mass spectrometry so that an accurate evaluation of the effectiveness of washing may be made.

It is found that films and fibers of poly(N-acetyl-D-glucosamine) cast from hexafluoroisopropyl alcohol or hexafluoroacetone sesquihydrate are not degraded by deionized water after 10 days exposure at ambient temperature. The same films immersed in a phosphate buffer containing 1500 units/ml of lysozyme at 37° C begin to degrade, although after 15 days, the films maintain their structure but are substantially degraded when observed by a microscope.

Both films and fibers of poly(N-acetyl-D-glucosamine) may be stretched, conveniently using heat, to orient the structure. Films and fibers of oriented structure are usually much stronger than unoriented films or fibers.

As the scope of this invention is broad, it is illustrated by the following typical examples in which temperatures are centigrade, and parts are by weight unless clearly otherwise specified.

EXAMPLE 1

Purification of Chitin

A commercial grade of chitin (Cal-Biochemicals) was finely ground in a ball mill overnight to pass a 6 mm screen and be retained by a 1 mm screen. 149 g. of this finely ground material was decalcified by extracting with 825 ml. of 2N HCl at 4° C for 48 hours, in a flask stirred with a magnetic stirrer. The material was collected by centrifugation and washed repeatedly with water until neutral. The ash content was 0.4–0.5%. The decalcified chitin was then stirred at room temperature with 1500 ml. of 90% formic acid overnight. The mixture was centrifuged and the residue repeatedly washed with water. The washed chitin was then suspended in 2 liters of 10% NaOH solution and heated at 90°–100° C. for 2.5 hours. The solution was filtered, the cake washed with water until neutral, washed several times with absolute ethanol and ether, and dried at 40° C. under reduced pressure; yield 66 g. of poly(N-acetyl-D-glucosamine). Infrared spectrum (KBr pellet) shows bands at 3500 cm$^{-1}$ (S), 2900 (W), 1652 (S), 1619 (S), 1550 (S), 1370 (S), 1300 (M), 1070 (Broad). (S is strong, M is medium, W is weak).

EXAMPLE 2

Poly(N-Acetyl-D-Glucosamine) Matrix

Membranes of poly(N-acetyl-D-glucosamine) were prepared by dissolving poly(N-acetyl-D-glucosamine) from Example 1 in each of hexafluoroacetone sesquihydrate (1.4% solution) and hexafluoroisopropanol (2% solution), and casting on a glass plate. The last traces of solvent were evaporated off in a vacuum. The films were tough, transparent, non-tacky, flexible and were quite pliable when hydrated yet retained adequate strength to resist manipulation. The membranes showed no hydrolysis after exposure to water for 5 days. In the presence of lysozyme, however, the films were degraded slowly. The films as cast are suitable for use as absorbable barrier layers in surgery. They may be split and twisted to form sutures.

EXAMPLE 3

Dry Spinning Sutures

A spinning solution is prepared by dissolving three parts by weight of the poly(N-acetyl-D-glucosamine) from Example 1 in 97 parts by weight of hexafluoroisopropyl alcohol. The solution is heated to about 55° C.

with gentle stirring until the solution is accomplished. The thus formed solution is pumped through a spinnerette having 16 capillaries 100 microns in diameter and the spun fibers are passed through a nitrogen atmosphere until at least partially cool, and self-sustaining. The yarn formed is wound on a bobbin and stored hot under vacuum for several days. The yarn is then stretched to insure orientation and braided into a suture which is needled, wrapped on a reel, and stored in an open pack. The suture is sterilized by autoclaving at 30 lbs. steam for 15 minutes, and packaged in strippable envelopes.

EXAMPLE 4

Wet Spinning Sutures

A 3% solution of poly(N-acetyl-D-glucosamine) from Example 1 is prepared in hexafluoroacetone sesquihydrate by dissolving therein with heating and stirring. The resulting spinning dope is pumped through a 20 hole spinnerette having 100 microns capillary diameter into an acetone bath which is maintained below room temperature. The coagulated wet gel is pulled away from the spinning head and washed countercurrently with acetone. The coagulated gel is washed with additional acetone, then wound on a reel and subjected to vacuum at 50° C. until substantially all of the solvent is removed.

The yarn is hot stretched, then braided into a size 2/0 suture, needled, sterilized by autoclaving as in the preceding example, packaged and held for use.

Sutures from Examples 3 and 4, when used to sew up wounds in living tissue, are found to hold the tissues in place until healing sufficient to be self-supporting has accrued, and the sutures are later absorbed.

The surgical elements of poly(N-acetyl-D-glucosamine) can be sterilized by conventional techniques such as autoclaving in the presence of live steam, or by dry heat, or ethylene oxide diluted with enough halofluoroalkane or carbon dioxide to be non-explosive, or by radiation by X-rays, gamma rays from cobalt, etc.

For human use, all surgical elements are to be sterile at time of use. For animal use, sterility should be maintained.

We claim:

1. A surgical prosthesis comprising non-absorbable filaments shaped as a living tissue reinforcing element, and mixed with and coacting with said non-absorbable filaments, in at least a part of the element, a structure consisting essentially of poly(N-acetyl-D-glucosamine), whereby on implantation in living tissue, the poly(N-acetyl-D-glucosamine) is absorbed by the living tissue which replaces the poly(N-acetyl-D-glucosamine) and interlocks with the non-absorbable filaments, said prosthesis being sterile at time of implantation.

2. The prosthesis of claim 1 in which the reinforcing element comprises a non-absorbable strand fabric mesh section, and interwoven and graded thereinto, bicomponent strands in a graded transition portion, the individual strands of which are of proportionately increasing poly(N-acetyl-D-glucosamine) and decreasing non-absorbable filament composition, at increasing distances from said non-absorbable strand fabric mesh section.

3. An absorbable prosthesis for the anastomosis of vessels in the tissue of a living mammal consisting essentially of a hollow cylinder of poly(N-acetyl-D-glucosamine), having an inner diameter approximately the same as the inner diameter of the subject vessel, and a smooth outer surface of a diameter which is insertable in said vessel when stretched, whereby one end of a vessel from traumatic or surgical severance may be emplaced over each end of said cylinder, and fixedly positioned thereon, said cylinder being open to and permitting the flow of body fluids and being absorbable by living mammalian tissue.

* * * * *